United States Patent [19]

Guo

[11] Patent Number: 6,156,861

[45] Date of Patent: Dec. 5, 2000

[54] CARBAMATE-FUNCTIONAL ALLYL MONOMERS AND POLYMERS THEREFROM

[75] Inventor: Shao Hua Guo, West Goshen, Pa.

[73] Assignee: Arco Chemical Technology, L.P., Greenville, Del.

[21] Appl. No.: 09/535,175

[22] Filed: Mar. 27, 2000

Related U.S. Application Data

[62] Division of application No. 09/166,803, Oct. 6, 1998, Pat. No. 6,075,108.

[51] Int. Cl.[7] .................................................. C08F 126/00
[52] U.S. Cl. ........................... 526/312; 526/297; 526/301; 526/304; 526/305; 526/307.2; 526/310; 526/314; 526/318.4; 526/319; 526/332; 526/340.4
[58] Field of Search ....................................... 526/312, 297, 526/301, 304, 305, 307.2, 310, 314, 318.4, 319, 332, 340.2

[56] References Cited

U.S. PATENT DOCUMENTS

| | | | |
|---|---|---|---|
| 3,479,328 | 11/1969 | Nordstrom | 260/86.1 |
| 3,674,838 | 7/1972 | Nordstrom | 260/482 |
| 3,852,233 | 12/1974 | Lindenmann | 260/29.6 TA |
| 4,126,747 | 11/1978 | Cowherd, III et al. | 520/166 |
| 4,279,833 | 7/1981 | Culbertson et al. | 260/464 |
| 5,037,700 | 8/1991 | Davis | 428/414 |
| 5,356,669 | 10/1994 | Rehfuss et al. | 427/407.1 |
| 5,382,642 | 1/1995 | Guo | 526/333 |
| 5,552,497 | 9/1996 | Taylor et al. | 525/456 |
| 5,605,965 | 2/1997 | Rehfuss et al. | 525/100 |
| 5,639,554 | 6/1997 | McGee et al. | 428/423.1 |
| 5,709,950 | 1/1998 | Burgman et al. | 428/423.1 |

*Primary Examiner*—Helen L. Pezzuto
*Attorney, Agent, or Firm*—Jonathan L. Schuchardt

[57] ABSTRACT

Carbamate-functional allyl monomers and methods for making them are disclosed. The monomers, which are easy to prepare, readily polymerize with common ethylenic monomers to give low-molecular-weight resins without the need for solvents or chain-transfer agents. Coatings made from the resins should have good durability, good acid etch resistance, good mar resistance, high gloss, and high DOI.

8 Claims, No Drawings

CARBAMATE-FUNCTIONAL ALLYL MONOMERS AND POLYMERS THEREFROM

This is a division of application Ser. No. 09/166,803, filed Oct. 6, 1998, now U.S. Pat. No. 6,075,108.

FIELD OF THE INVENTION

The invention relates to carbamate-functional allyl monomers and polymer resins made from the monomers. The resins are useful intermediates in many thermoset polymer applications, and they are particularly valuable for automotive and industrial coatings.

BACKGROUND OF THE INVENTION

Carbamate-functional monomers are known—though somewhat esoteric—components for making coating resins. They are sometimes used to modify the properties of the more-familiar acrylic and vinyl coating resins when improved adhesion, flexibility, or chemical resistance is needed. While many classes of carbamate-functional monomers have been described, high cost and challenging synthetic hurdles have inhibited their general use or commercialization.

Carbamyloxy acrylate and carbamoxy vinyl monomers, such as those described in U.S. Pat. Nos. 3,674,838, 4,126,747, and 4,279,833, are two kinds of carbamate-functional monomers now known. While these can be made several ways, each method requires expensive starting materials (e.g., hydroxyalkyl acrylate monomers) or hazardous reagents (e.g., phosgene or acryoyl chloride). One reasonably convenient synthesis reacts a hydroxyalkyl acrylate with urea, but this method's high reaction temperature requirement (>130° C.) promotes unwanted polymerization of the acrylic moiety.

Carbamate-functional polymers have the potential to boost the quality of melamine coatings. Traditionally, melamine coatings are reaction products of hydroxyacrylic resins and melamine resins. While these coatings have good hardness and mar resistance, they have relatively poor resistance to acid etching. In contrast, traditional polyurethane coatings have good acid etch resistance but can lack adequate hardness or mar resistance. Carbamate-functional polymers could give melamine coatings enough urethane character to overcome the acid etch problems of traditional melamine coatings.

Recently, scientists at BASF Corporation and PPG Industries, Inc. described coating compositions containing polymers with carbamate functionality (see, e.g., U.S. Pat. Nos. 5,356,669, 5,605,965, 5,639,554, 5,552,497 and 5,709,950). The carbamate-functional polymers are said to give coatings with good durability, good acid etch resistance, high gloss, and high DOI, and have particular value for automotive coatings. The carbamate-functional polymers used here, however, require a non-trivial synthesis and/or expensive starting materials. U.S. Pat. No. 5,356,669, for example, makes a carbamate-functional polymer by first copolymerizing ethyl hexyl acrylate with unsaturated m-tetramethyl xylene isocyanate (a commercially available but expensive monomer), and then reacting the isocyanate-functional copolymer with hydroxypropyl carbamate (see column 6, lines 1–42 of the reference).

In another method (see column 7, line 55 to column 8, line 24 of the '669 patent), the carbamate-functional polymer is made by first copolymerizing styrene and other monomers, including a hydroxy-functional acrylic monomer. The acrylic copolymer is then heated with urea in the presence of a metal carbalate catalyst to convert the resin's hydroxyl groups to carbamate groups. A disadvantage of this approach is the need to use a solvent (e.g., xylene/amyl acetate) or a chain-transfer agent in preparing the resin to keep the polymer molecular weight low. The relatively high cost of hydroxy-functional acrylic monomers is an added drawback.

Ideally, carbamate-functional monomers would be easy to prepare without unwanted side reactions, such as polymerization of acrylic moieties. Preferably, the carbamate-functional monomers would readily polymerize with other ethylenic monomers (e.g., styrene and acrylic monomers). A valuable monomer would enable the synthesis of low-molecular-weight resins useful for making thermoset compositions, especially low-VOC coatings. Ideally, the resins could be made without solvents or chain-transfer agents.

SUMMARY OF THE INVENTION

The invention is a carbamate-functional allyl monomer and a method for making it. The monomer has the structure:

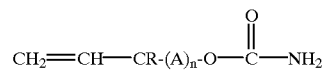

in which R is hydrogen or $C_1$–$C_{10}$ alkyl or aryl, A is oxyalkylene, and n has a value from 1 to 50. A simple, valuable way to make the monomer comprises heating an alkoxylated allylic alcohol with urea under conditions effective to produce the carbamate-functional allyl monomer.

The monomers readily homopolymerize or copolymerize with ethylenic monomers (e.g., styrene and acrylates) to give low-molecular-weight, carbamate-functional resins, which are particularly valuable for making thermoset coatings. Accordingly, the invention includes polymer resins and a process for making them. The resins comprise recurring units of a carbamate functional allyl monomer of the structure above in which n has a value from 0 to 50, and optionally, recurring units of one or more ethylenic monomers.

The carbamate-functional monomers and polymer resins of the invention offer surprising and valuable advantages. First, the monomers are easy to prepare, and unwanted side reactions do not complicate their synthesis. In addition, the monomers readily homopolymerize or copolymerize with common ethylenic monomers. Finally, the monomers polymerize in the absence of solvents or chain-transfer agents to give low-molecular-weight resins that are particularly useful for low-VOC coatings. Coatings made from the resins should have good durability, good acid etch resistance, good mar resistance, high gloss, and high DOI.

DETAILED DESCRIPTION OF THE INVENTION

Carbamate-functional allyl monomers of the invention have the structure:

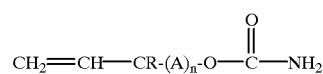

in which R is hydrogen or $C_1$–$C_{10}$ alkyl or aryl, A is oxyalkylene, and n has a value from 1 to 50. Oxyalkylene groups include, for example, oxyethylene, oxypropylene, oxybutylenes, and the like, and combinations of these.

Preferred monomers include one or more oxyalkylene groups selected from oxyethylene and oxypropylene. The average number of oxyalkylene groups in the monomer is n, which ranges from 1 to 50. Preferably, n has value from 1 to 10. Particularly preferred are monomers in which R is hydrogen, A is oxyethylene or oxypropylene, and n has a value from 1 to 5.

The invention includes a simple method for making the monomers. The method comprises heating an alkoxylated allylic alcohol with urea under conditions effective to produce the carbamate-functional allyl monomer. Suitable alkoxylated allylic alcohols are well known in the art (see, for example, U.S. Pat. No. 5,382,642, the teachings of which are incorporated herein by reference). They can be made by reacting allylic alcohols (e.g., allyl alcohol) with epoxides in the presence of an acidic or basic catalyst. Generally, the method of the invention requires heating. Preferably, the alkoxylated allylic alcohol and urea are heated at a temperature within the range of about 60° C. to about 300° C. A more preferred range is about 100° C. to about 250° C.; most preferred is the range from about 130° C. to about 200° C. Ammonia, a by-product from the reaction, is removed from the reaction mixture by any desired method The method described above is especially valuable for reacting urea with alkoxylated allylic alcohols with an average of one or two oxyalkylene units. Because the boiling points of these alcohols are at least as high as the required reaction temperature, pressurized reactors are not needed. Propoxylated allyl alcohol (ave. of 1.0 oxypropylene units), for example, has a boiling point of about 145° C. In contrast, the method would not be as practical for making allyl carbamate (from allyl alcohol and urea) because the temperature required for good reactivity exceeds the boiling point of allyl alcohol, and a pressurized reactor would be needed.

The carbamate-functional allyl monomers can also be made using conventional methods. For example, the alkoxylated allylic alcohol can be reacted with phosgene followed by neutralization with ammonia to give a carbamate monomer of the invention. A drawback of this method is the need to handle phosgene.

The carbamate-functional allyl monomers are easy to prepare. The hard-to-handle reagents of prior methods (phosgene, acryloyl chloride) are replaced by a relatively innocuous alternative: urea. Moreover, because allylic double bonds are relatively unreactive (compared with, e.g., acrylic ones), unwanted side reactions do not complicate monomer synthesis.

The invention includes polymer resins made from the carbamate-functional monomers and a process for making the resins. The resins comprise recurring units of a carbamate-functional allyl monomer and, optionally, one or more ethylenic monomers. The carbamate-functional allyl monomer has the structure:

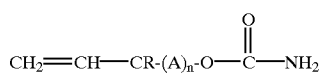

in which R is hydrogen or $C_1$–$C_{10}$ alkyl or aryl, A is oxyalkylene, and n has a value from 0 to 50. Preferably, A is one or more oxyalkylene groups selected from oxyethylene and oxypropylene. The average number of oxyalkylene groups in the monomer is n, which ranges from 0 to 50. Preferably, n has value from 1 to 10. Particularly preferred are monomers in which R is hydrogen, A is oxyethylene or oxypropylene, and n has a value from 1 to 5.

The polymer resin optionally includes recurring units of an ethylenic monomer. Suitable ethylenic monomers are copolymerizable with the allylic double bond of the carbamate-functional monomer. Preferably, the ethylenic monomer is one or more selected from the group consisting of vinyl aromatic monomers, acrylates, acrylic acids, acrylamides, vinyl ethers, vinyl esters, vinyl carbonates, vinyl halides, vinylidene halides, unsaturated anhydrides, unsaturated diacids, unsaturated nitriles, allylic alcohols, alkoxylated allylic alcohols, allyl esters, allyl ethers, allyl carbonates, conjugated dienes, and mixtures thereof. Particularly preferred ethylenic monomers are vinyl aromatic monomers (especially styrene), acrylates, and acrylic acids.

The relative proportion of carbamate-functional allyl monomer and ethylenic monomer used can vary over a wide range. The most desirable proportion will depend on many factors within the skilled person's discretion, including, for example, the nature of the carbamate-functional monomer and ethylenic monomer(s), the relative reactivities of the monomers, the desired level of crosslinkable carbamate groups, the intended end use, the desired coating properties, and other factors. Preferably, however, the polymer resins comprise from about 30 to about 70 wt. % of the carbamate-functional allyl monomer and from about 30 to about 70 wt. % of the ethylenic monomer(s).

The invention includes a process for making the polymer resins. The process comprises polymerizing a carbamate-functional allyl monomer as described above, optionally with one or more ethylenic monomers. The process is performed using well-known free-radical polymerization techniques. Suitable polymerization processes include bulk, solution, suspension, and emulsion techniques, with bulk polymerization being preferred. In a typical process, the monomers are heated in the presence of a free-radical initiator at a temperature effective to polymerize the monomers. The reaction is preferably performed at a temperature within the range of about 30° C. to about 300° C.; a more preferred range is from about 80° C. to about 200° C. Suitable free-radical initiators are known in the art, and include peroxides and azo compounds; peroxides are preferred. Preferably, the monomers and free-radical initiator are added gradually and at a decreasing rate to a reaction mixture that is heated to the desired reaction temperature. After the polymerization is complete, residual unreacted monomers are removed by vacuum stripping, wiped-film evaporation, or similar techniques.

The carbamate-functional polymer resins of the invention preferably have number average molecular weights within the range of about 500 to about 50,000, more preferably from about 500 to about 10,000; most preferred is the range from about 1000 to about 5000.

An advantage of the invention is the ability to make low-molecular-weight coating resins from common ethylenic monomers in the absence of solvents or chain-transfer agents. The allyl group of the carbamate-functional monomer is the key. While resin producers routinely use solvents or chain-transfer agents to keep resin molecular weight low, solvents are costly to remove and chain-transfer agents add cost, introduce unwanted odors, or detract from resin performance. The carbamate-functional allyl monomer, because of its relatively low reactivity, overcomes the need for solvents or chain-transfer agents.

The carbamate-functional polymer resins are useful for making coatings. The coatings are made by reacting the resins with crosslinking agents that contain functional groups able to react with the carbamate groups. Suitable crosslinking agents are known in the art and are taught, for example, in U.S. Pat. No. 5,356,669, the teachings of which are incorporated herein by reference. Generally, suitable crosslinking agents will have methylol, methylalkoxy, isocyanate, siloxane, cyclic carbonate, or anhydride groups. Examples include melamine resins (e.g., melamine-formaldehyde resins such as CYMEL 303 resin, a product of Cytec), urea resins (e.g., alkoxyureas, urea-formaldehyde resins), methylol-containing phenol-formaldehyde adducts, polyanhydrides, polysiloxanes, and the like, and mixtures thereof. Particularly preferred are melamine and urea resins.

The polymer resin and crosslinking agent can be reacted in any suitable way to make coatings. For example, they can be used in substantially solid form (as in making powder coatings), or as a solution or dispersion. Preferably, the polymer resin and crosslinking agent are reacted in an organic solvent that will dissolve both reactants. Useful organic solvents include alcohols, esters, ethers, ketones, amides, sulfoxides, aromatic and aliphatic hydrocarbons, halogenated hydrocarbons, amides, or the like, and mixtures thereof. Water can also serve as the solvent or as a cosolvent with one or more organic solvents. When a solvent is used, the resin/crosslinking agent solution is applied to a surface and the solvent is allowed to evaporate at room or elevated temperature until a cured coating is obtained.

If desired, a curing catalyst can be included to accelerate the reaction between the carbamate groups of the polymer resin and the crosslinking agent. Such catalysts are described in U.S. Pat. No. 5,356,669. Any desired technique can be used to apply the coatings, including, for example, spraying, dipping, brushing, rolling, or the like.

Coatings made using the polymer resins can be used as pigmented basecoats, as clearcoats, or as both in a composite color-plus-clear coating system as described in U.S. Pat. Nos. 5,356,669 and 5,709,950. Because the coatings derive from carbamate-functional resins, they are expected to have good durability, good acid etch resistance, good mar resistance, high gloss, and high DOI.

The following examples merely illustrate the invention. Those skilled in the art will recognize many variations that are within the spirit of the invention and scope of the claims.

EXAMPLE 1

Preparation of Allyl Carbamate

A two-liter, three-neck, round-bottom flask equipped with thermometer, addition funnel, and magnetic stirrer is charged with aqueous ammonium hydroxide (1000 g of 30% $NH_4OH$), and the solution is chilled in an ice bath. Allyl chloroformate (492 g) is charged to the addition funnel, and is then added dropwise over 6 h to the flask while maintaining the reaction temperature below 15° C. After the addition is complete, the stirred mixture is allowed to warm to room temperature overnight.

The reaction mixture is chilled to 5° C., stirred at that temperature for 2 h, and filtered to collect the solid product. The filtrate is concentrated by vacuum distillation (to remove water), and the residue is cooled to 25° C. and filtered to collect more solids. The concentration process is repeated, and more solids are collected. The combined solids are purified by vacuum distillation (b.p. 62–67° C., about 0.7 to 1.3 mm Hg) The resulting product, allyl carbamate, is obtained in 84% yield.

EXAMPLE 2

Preparation of a Carbamate-Functional Polymer Resin

Allyl carbamate (310 g, as prepared in Example 1) is charged to a one-liter, stainless-steel reactor equipped with agitator, steam heating jacket, temperature controller, nitrogen purge device, vacuum distillation device, and addition pump. Methyl methacrylate (70.1 g), n-butyl acrylate (58.4 g), n-butyl methacrylate (140.3 g), styrene (86.5 g), methacrylic acid (7.0 g), and tert-amylperoxy-2-ethyihexanoate (19.9 g) are mixed and cooled to 5° C. After purging the chilled mixture with nitrogen, a portion (51.4 g) is charged to the reactor; the rest is transferred to the addition pump. After purging the reactor three times with nitrogen, it is sealed, and the contents are heated to 135° C. The monomer mixture is added to the reactor gradually at a decreasing rate over 5 h at 135° C. The addition rates are as follows: first hour: 98.3 g; second hour: 86.6 g; third hour: 73.3 g; fourth hour: 49.2 g; fifth hour: 23.4 g; sixth hour: 23.4 g.

After the addition is complete, the reaction continues at 135° C. for another 0.5 h. The reactor is cooled, and the product is collected. Residual monomers are removed by wiped-film evaporation. The resulting carbamate-functional polymer resin (550 g) has Mn=3200; Mw=7900.

EXAMPLE 3

Preparation of Allyl Ethoxy Carbamate

A 100-mL flask equipped with a thermometer, reflux condenser, and magnetic stirrer is charged with ethoxylated allyl alcohol (average of 1.0 oxyethylene group, 36 g) and urea (10 g). The mixture is heated using an oil bath to reflux (about 160° C.) for 6 h. The reaction mixture is then allowed to cool briefly and is poured into water (100 mL). The product is extracted into methylene chloride (100 mL) and is concentrated. Vacuum distillation (b.p. 173–176° C. at 1 mm Hg) gives allyl ethoxy carbamate (20 g) suitable for use in making carbamate-functional resins.

EXAMPLE 4

Preparation of a Carbamate-Functional Polymer Resin

The procedure of Example 2 is generally followed, except that allyl ethoxy carbamate, prepared as in Example 3, is used instead of allyl carbamate. The expected product is a carbamate-functional polymer resin.

EXAMPLE 5

Coating from a Carbamate-Functional Polymer Resin

The carbamate-functional resin of Example 2 (36 g) is dissolved in a mixture of n-butyl acetate (16 g) and n-butyl alcohol (8 g). CYMEL 303 resin (product of Cytec, 15 g), CYCAT 600 catalyst (product of Cytec, 0.5 g), and Dow 57 defoamer (product of Dow Corning, 0.027 g) are added to the mixture. The solution is diluted with n-butyl acetate/n-butyl alcohol solvent mixture to a viscosity of 42 s in EZ Cup #2. The solution is then applied to stainless-steel panels and dried at 140° C. for 0.5 h to give a hard, glossy coating.

The preceding examples are meant only as illustrations; the following claims define the scope of the invention.

I claim:

1. A process which comprises polymerizing:

(a) a carbamate-functional allyl monomer of the structure:

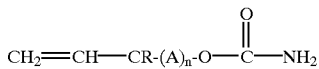

in which R is hydrogen or $C_1$–$C_{10}$ alkyl or aryl, A is oxyalkylene, and n has a value from 0 to 50; and (b) optionally, one or more ethylenic monomers selected from the group consisting of vinyl aromatic monomers, acrylates, acrylic acids, acrylamides, vinyl ethers, vinyl esters, vinyl carbonates, vinyl halides, vinylidene halides, unsaturated anhydrides, unsaturated diacids, unsaturated nitriles, allylic alcohols, alkoxylated allylic alcohols, allyl esters, allyl ethers, allyl carbonates, conjugated dienes, and mixtures thereof.

2. The process of claim 1 wherein A is selected from the group consisting of oxyethylene, oxypropylene, and mixtures thereof.

3. The process of claim 1 wherein n has a value from 1 to 10.

4. The process of claim 1 wherein R is hydrogen, A is oxyethylene or oxypropylene, and n has a value from 1 to 5.

5. The process of claim 1 that yields a polymer resin having a number average molecular weight within the range of about 500 to about 10,000.

6. The process of claim 1 wherein the ethylenic monomer is selected from the group consisting of vinyl aromatic monomers, acrylates, and acrylic acids.

7. The process of claim 1 wherein the ethylenic monomer is styrene.

8. A process which comprises polymerizing:

(a) a carbamate-functional allyl monomer of the structure:

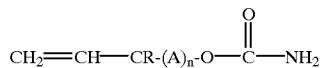

in which R is hydrogen, A is oxyethylene or oxypropylene, and n has a value from 1 to 5; and (b) an ethylenic monomer selected from the group consisting of vinyl aromatic monomers, acrylates, and acrylic acids.

* * * * *